(12) United States Patent
Wu et al.

(10) Patent No.: US 11,324,590 B2
(45) Date of Patent: May 10, 2022

(54) COLLAPSING PUSH INJECTOR WITH HYDRAULIC DAMPING

(71) Applicant: Alcon Inc., Fribourg (CH)

(72) Inventors: Yinghui Wu, Cedar Hill, TX (US); Len Takudzwa Magara, Ithica, NY (US); Sudarshan B. Singh, Euless, TX (US); Douglas Brent Wensrich, Bedford, TX (US); Todd Taber, Keller, TX (US)

(73) Assignee: Alcon Inc., Fribourg (CH)

( * ) Notice: Subject to any disclaimer, the term of this patent is extended or adjusted under 35 U.S.C. 154(b) by 221 days.

(21) Appl. No.: 16/711,981

(22) Filed: Dec. 12, 2019

(65) Prior Publication Data

US 2020/0197166 A1   Jun. 25, 2020

Related U.S. Application Data (60) Provisional application No. 62/782,041, filed on Dec. 19, 2018.

(51) Int. Cl.
  *A61F 2/16*  (2006.01)
  *A61F 2/48*  (2006.01)

(52) U.S. Cl.
  CPC ............ *A61F 2/1672* (2013.01); *A61F 2/167* (2013.01); *A61F 2/1667* (2013.01); *A61F 2/484* (2021.08); *A61F 2002/1683* (2013.01); *A61F 2002/16905* (2015.04); *A61F 2230/0069* (2013.01)

(58) Field of Classification Search
  CPC ...... A61F 2/1672; A61F 2/1667; A61F 2/167; A61F 2002/16905; A61F 2230/0069; A61F 2002/1682; A61F 2/1662; A61F 2/16; A61M 2205/581
  USPC .......... 623/6.12, 6.11, 6.13; 606/4, 5, 6, 107
  See application file for complete search history.

(56) References Cited

U.S. PATENT DOCUMENTS

| | | | |
|---|---|---|---|
| 9,095,425 B2 | 8/2015 | Meyer | |
| 9,364,316 B1 | 6/2016 | Kahook et al. | |
| 2008/0086146 A1 | 4/2008 | Ishii et al. | |
| 2009/0036827 A1* | 2/2009 | Cazzini | A61F 9/0017 604/60 |
| 2011/0295264 A1 | 12/2011 | Cole et al. | |
| 2014/0200588 A1* | 7/2014 | Anderson | A61F 2/1678 606/107 |
| 2014/0276898 A1* | 9/2014 | Novak | A61F 2/148 606/107 |
| 2017/0119522 A1* | 5/2017 | Auld | A61F 2/167 |
| 2017/0319332 A1 | 11/2017 | Kahook et al. | |

FOREIGN PATENT DOCUMENTS

| | | |
|---|---|---|
| EP | 2332501 A1 | 6/2011 |
| WO | 2010039841 A1 | 4/2010 |

* cited by examiner

*Primary Examiner* — Tan-Uyen T Ho
*Assistant Examiner* — Bridget E. Rabaglia (57) ABSTRACT

Systems, methods, and devices for inserting an intraocular lens (IOL) assembly into an eye may be provided. A device for delivery of the IOL into the eye may include a housing; a nozzle operatively coupled to the housing; a first cylinder movably disposed within the housing; a second cylinder movably disposed within the housing, wherein the second cylinder is in fluid communication with the first cylinder; a plunger at least partially and movably disposed within the first cylinder; and a shaft movably disposed within the second cylinder, wherein the shaft is configured to move toward the lens component.

20 Claims, 11 Drawing Sheets

FIG.9C

COLLAPSING PUSH INJECTOR WITH HYDRAULIC DAMPING

TECHNICAL FIELD

The present disclosure generally relates to eye surgery and, more particularly, embodiments may generally relate to systems, methods, and devices for inserting an intraocular lens (IOL) into an eye.

BACKGROUND

The human eye can suffer a number of maladies causing mild deterioration to complete loss of vision. While contact lenses and eyeglasses can compensate for some ailments, ophthalmic surgery may be required for others. Generally, ophthalmic surgery may be classified into posterior segment procedures, such as vitreoretinal surgery, and anterior segment procedures, such as cataract surgery. Vitreoretinal surgery may address many different eye conditions, including, but not limited to, macular degeneration, diabetic retinopathy, diabetic vitreous hemorrhage, macular hole, detached retina, epiretinal membrane, and cytomegalovirus retinitis.

For cataract surgery, a surgical procedure may require incisions and insertion of tools within an eye to replace the clouded lens with an intraocular lens (IOL). An insertion tool can be used for delivery of the IOL into the eye. By way of example, the insertion tool may include a plunger for forcing the IOL out of the nozzle of the insertion tool. In some instances, the IOL may be pre-loaded in the insertion tool. In other instances, a separate bay may be loaded into the insertion tool. The plunger may engage the IOL to advance the IOL from the bay, through the nozzle, and into the eye. The bay (or insertion tool) may include a folding chamber configured to cause the IOL to fold, for example, when the IOL advances through the folding chamber. In some instances, a separate action may cause folding of the IOL.

Delivery of the IOL from the insertion tool can be a multi-step process. For example, the delivery may include two stages, which may be referred to as an advancing stage and a delivery stage. In the advancing stage, the IOL can be advanced from a storage position in the bay to a dwell position. The IOL may be pre-folded or may be folded when advanced from the storage position to the dwell position. At the dwell position, advancement of the IOL may be halted. With the nozzle positioned in the eye, the IOL may then be further advanced from the dwell position, in the delivery stage, which may include advancing the IOL through the nozzle and into the eye. However, this multi-step process can be problematic. For example, the user may be required to make a judgement on whether the IOL has been advanced to a proper dwell position in the advancing stage. Thus, the exact position of the IOL in the dwell position can vary from procedure to procedure. In addition, multiple actions by the user can increase time in the operation room and, thus, increase cost of the procedure.

SUMMARY

In an exemplary embodiment, the present disclosure provides an apparatus for delivery of a lens component into an eye. The apparatus includes a housing; a nozzle operatively coupled to the housing; a first cylinder movably disposed within the housing; a second cylinder movably disposed within the housing, wherein the second cylinder is in fluid communication with the first cylinder; a plunger at least partially and movably disposed within the first cylinder; and a shaft movably disposed within the second cylinder, wherein the shaft is configured to move toward the lens component.

In another exemplary embodiment, the present disclosure provides an apparatus for delivery of a lens component into an eye. The apparatus includes a housing comprising a threaded passage; a nozzle operatively coupled to the housing; a threaded sleeve disposed concentrically within the threaded passage; and a plunger assembly coupled to the threaded sleeve, the plunger assembly comprising: a first cylinder; a second cylinder, wherein the second cylinder is in fluid communication with the first cylinder; a plunger at least partially disposed within the first cylinder; and a shaft movably disposed within the second cylinder, wherein the shaft is configured to move toward the lens component.

In another exemplary embodiment, the present disclosure provides a method for delivery of a lens component into an eye. The method includes providing an insertion tool, wherein the insertion tool comprises a housing; a first cylinder movably disposed within the housing, wherein the first cylinder comprises a hydraulic fluid; a second cylinder movably disposed within the housing, wherein the second cylinder is in fluid communication with the first cylinder; a plunger at least partially disposed within the first cylinder; and a shaft movably disposed within the second cylinder, wherein the shaft is configured to move towards the lens component. The method further includes actuating the plunger to move the hydraulic fluid from the first cylinder into the second cylinder to axially move the shaft to drive the lens component in the nozzle.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

These drawings illustrate certain aspects of some of the embodiments of the present disclosure and should not be used to limit or define the disclosure.

DETAILED DESCRIPTION

For the purposes of promoting an understanding of the principles of the present disclosure, reference will now be made to the implementations illustrated in the drawings and specific language will be used to describe them. It will nevertheless be understood that no limitation of the scope of the disclosure may be intended. Any alterations and further modifications to the described devices, instruments, methods, and any further application of the principles of the present disclosure are fully contemplated as would normally occur to one skilled in the art to which the disclosure relates. In particular, it may be fully contemplated that the features, components, and/or steps described with reference to one or more implementations may be combined with the features, components, and/or steps described with reference to other implementations of the present disclosure. For simplicity, in some instances the same reference numbers are used throughout the drawings to refer to the same or like parts.

Embodiments may generally relate to eye surgery. More particularly, embodiments may generally relate to systems, methods, and devices for inserting an intraocular lens (IOL). Embodiments may include an insertion tool for preparation and delivery of the IOL into a patient's eye and allow for a sterile transfer of the IOL from storage until it is placed within the capsular bag of a patient.

Any suitable IOL may be used, including, but not limited to, IOLs that include a lens portion and haptic extensions. The haptic extensions may be side struts (or other suitable extensions) that extend from the lens portion to hold the lens portion in place when implanted in the eye. In at least one embodiment, the IOL may be modular. Embodiments of a modular IOL may include a base portion and a lens portion. The base portion may include the haptic extensions. The lens portion may be coupled to the base portion to form the modular IOL.

In many typical syringe or push type injectors, a user applied force may be directly proportional to an IOL travel speed. With these typical syringe or push type injectors, users may compensate (e.g., by increasing a pressing force on the plunger in an axial direction) to perceived higher forces during advancement as the IOL exits the nozzle, resulting in sudden ejection of the IOL. This can result in a sudden injection of the IOL into a patient's eye and can cause damage to the patient's eye.

Further, a large pressure release may occur when the IOL exits the nozzle. In some cases, this may cause the IOL to eject at a high velocity thereby reducing a user's control of the insertion tool. These pressure and force fluctuations may reduce a user control of the insertion tool and ultimately the IOL delivery.

Due to the sensitivity and delicacy of ocular tissues and structures, it may be desired to advance the IOL with acceptable peak speed and force. Embodiments of the present disclosure are directed to an advancement technique that utilizes a hydraulic mechanism that force-assists a user by allowing a controlled fluid flow through a small orifice.

Particular embodiments of the hydraulic mechanism(s) as described herein maintain a constant fluid flow rate without varying a user's force input. The hydraulic mechanism(s) may provide a steady force feedback to a user, and may limit occurrences of sudden ejection. In addition, the hydraulic mechanism(s) may allow an application of a reasonable amount of force throughout delivery of the IOL, thereby reducing a user's fatigue.

Certain embodiments may be directed to propelling the IOL in a controlled and consistent manner. An initial advancement to dwell may be performed via a rotation of the plunger via a head, knob, or cap that may include a geometry (e.g., ridges) that conforms to a user's fingers and/or thumb. This should improve ergonomic handling. The rotation of the head moves the plunger and the IOL toward the nozzle along a threaded interior portion (passage) of the housing, thereby reducing an overall length of the insertion tool. This overall length adjustment should also improve ergonomic handling. The overall length of the insertion tool before final implantation or delivery of the IOL may be optimized for syringe type insertion tool grip profiles and may allow a user to be as close to a patient's eye as possible while affording the user greater balance. The syringe type grip profile should allow single handed grip during advancement to implantation.

Once the IOL has reached the dwell position, the plunger may be unlocked. A user may rotate the head (e.g., clockwise) until the user hears a "click". This indicates that the plunger is unlocked and ready for the final advancement by a surgeon (i.e., injection of the IOL into a patient's eye). The final advancement of the IOL may be performed via an axial push of the plunger head.

Figure 1:
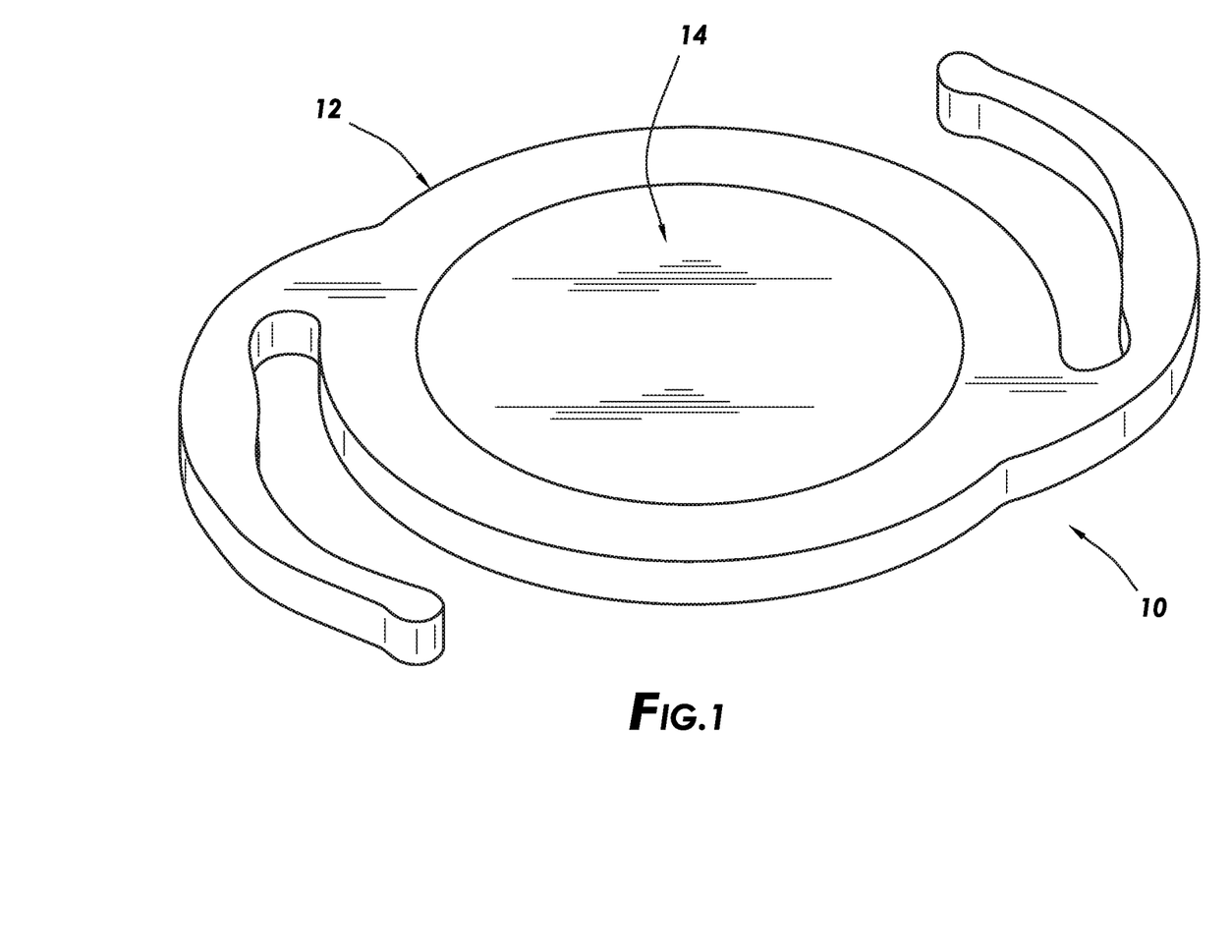
FIG. 1 illustrates a modular IOL with a lens portion positioned in a base portion in accordance with embodiments of the present disclosure.

FIG. 1 illustrates an embodiment of a modular IOL 10. The modular IOL 10 may be any suitable modular interocular lens. As illustrated, the modular IOL 10 may include a base portion 12 and a lens portion 14. In the illustrated embodiment, the lens portion 14 is positioned in the base portion 12. In operation, the modular IOL 10 can allow for the lens portion 14 to be modified or adjusted while leaving the base portion 12 in place, either intra-operatively or post-operatively. By way of example, the modular IOL 10 may be implanted into an eye. After implantation, the lens portion 14 may be modified, adjusted, and/or replaced while leaving the base portion 12 positioned in the eye. In at least one embodiment, the modular IOL 10 may be assembled in the eye. For example, the base portion 12 may first be implanted in the eye. The lens portion 14 may then be delivered into the eye and attached to the base portion 12.

Figure 2:
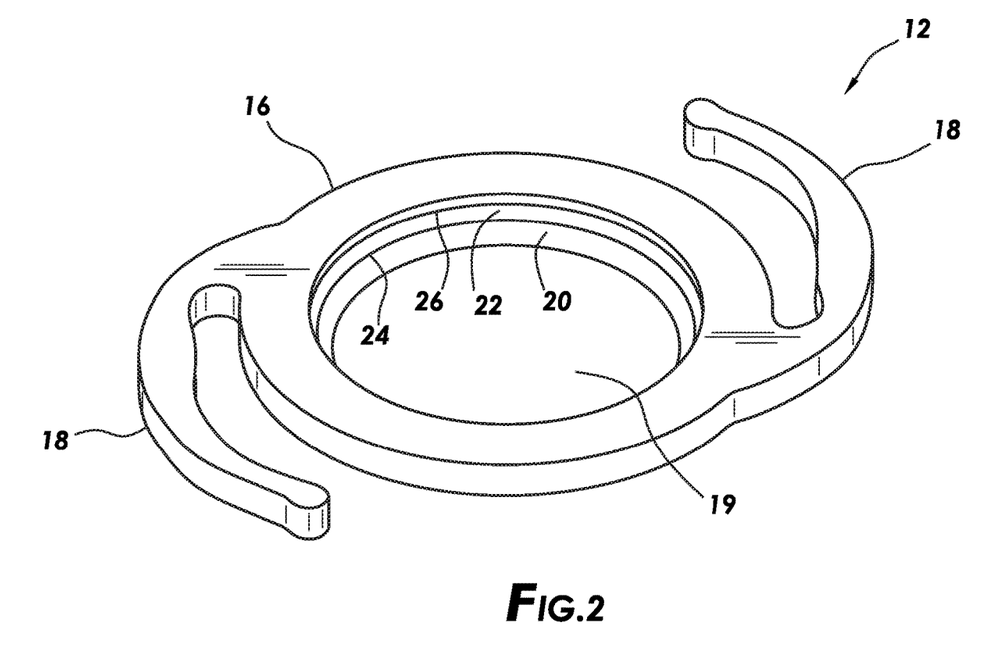
FIG. 2 illustrates a base portion of a modular IOL in accordance with embodiments of the present disclosure.

FIG. 2 illustrates the base portion 12 of the modular IOL 10 of FIG. 1 in accordance with embodiments of the present disclosure. In the illustrated embodiment, the base portion 12 includes a base 16 and haptic extensions 18. The haptic extensions 18 may be side struts (or other suitable extensions) extending from the base 16 that may stabilize the base portion 12 when it may be disposed within the patient's eye. In the illustrated embodiment, the base 16 may define a hole 19, which may be centrally located in the base 16 as shown on FIG. 2. While the hole 19 is shown as a through hole extending through the base 16, embodiments also contemplate hole 19 being a blind hole that does not extend through the base 16. For example, the base 16 may be a solid disc with the hole 19 being a blind hold that does not extend through the base 16, rather than an annular ring with the hole 19 extending through the base 16. Hole 19 may be defined by inner perimeter surface 20 of the base 16. In at least one embodiment, a recessed groove 22 is formed in inner perimeter surface 20. Recessed groove 22 may include a lower rim 24 and an upper rim 26. The upper rim 26 may have an insider diameter that is the same as or greater than the outside diameter of the lens portion 14 (excluding tabs 30 shown on FIG. 3) such that the lens portion 14 can rest inside the hole 19 of the base 16. All or a portion of the lower rim 24 can have an inside diameter that is less than the outside diameter of the lens portion 14 (excluding tabs 30 shown on FIG. 3) such that the lower rim 24 can act as a ledge or backstop for the lens portion 14 when placed in the hole 19 of the base 16. The base portion 12 may be unitary or may be formed from component parts that are combined or attached in any suitable manner.

Figure 3:
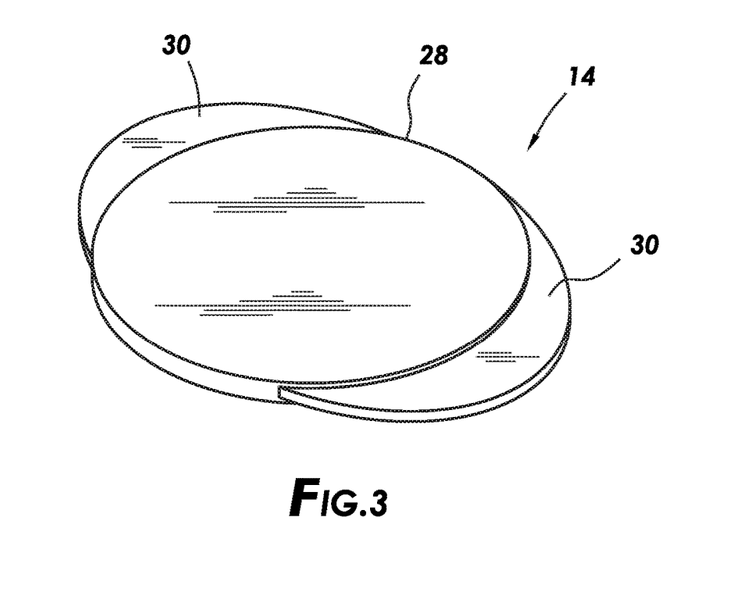
FIG. 3 illustrates a lens portion of a modular IOL in accordance with embodiments of the present disclosure.

With reference to FIG. 3, the lens portion 14 of the modular IOL 10 of FIG. 1 is illustrated in accordance with embodiments of the present disclosure. In the illustrated embodiments, the lens portion 14 includes an optic portion 28 and one or more tabs 30. While FIG. 3 illustrates two of the tabs 30, embodiments may include only one of the tabs 30 or alternatively three, four, or more of the tabs 30. In addition, the tabs 30 on the lens portion 14 may be the same or different from one another. The tabs 30 are shown as being fixed to the optic portion 28; however, it should be understood that one or more of the tabs 30 may be actuated to move from a compressed position for delivery into the hole 19 of the base 16 (e.g., shown on FIG. 2) to an uncompressed extended position for deployment into the recessed groove 22 of the base 16 (e.g., shown on FIG. 2), thus forming an interlocking connection between the base portion 12 and the lens portion 14. The outside curvature of the tabs 30 may have a radius conforming to the inside radius of the recessed groove 22. This arrangement should limit relative movement between the base portion 12 and the lens portion 14 once connected. In embodiments, a suitable optic portion 28 may be in a shape similar to that of a natural lens within the eye and made from a suitable material such as silicone, acrylic, and/or combinations thereof. While the optic portion 28 is shown as being circular, the optic portion 28 may be any suitable shape, such as oval or ellipsoidal, for example, with the tabs 30 positioned adjacent the long axis. This arrangement would thus define a gap between the edge of the optic portion 28 along its short axis and the inner perimeter surface 20 in the base 16. The gap may enable access for a probe or similar device to pry apart the lens portion 14 from the base portion 12 if separation were needed.

Figure 4:
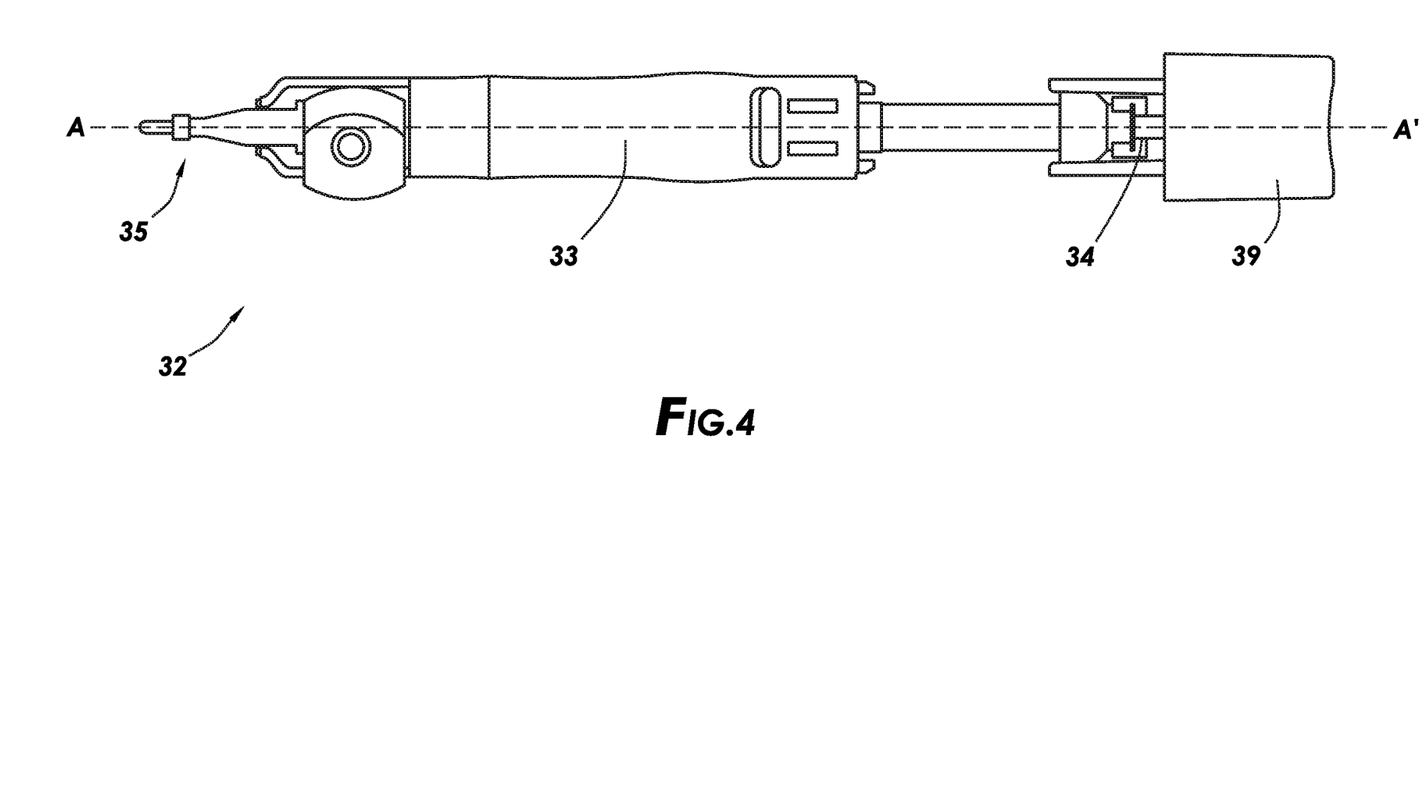
FIG. 4 is a top view of an insertion tool in accordance with embodiments of the present disclosure.

FIG. 4 illustrates a top view of an insertion tool 32 in accordance with exemplary embodiments. The insertion tool 32 may include a housing 33, a plunger 34 at least partially disposed axially within the housing 33, and a nozzle 35. The plunger 34 is slidably disposed within the housing 33 and may move axially along a longitudinal axis of the housing 33. A plunger head 39 may be coupled to the plunger 34 and may be positioned exterior to the housing 33. The nozzle 35 may be disposed on an end of the insertion tool 32 that is opposite to the plunger head 39, as shown. In other words, the plunger 34 and the plunger head 39 may extend from a first end of the housing 33, and the nozzle 35 may extend from a second opposite end of the housing 33, as shown. A user may depress the plunger head 39 to move the plunger 34 axially (toward the nozzle 35) within the housing 33. The housing 33 may be configured to receive the nozzle 35. In some embodiments, the nozzle 35 may be attachable the housing 33 so that the nozzle 35 can be coupled and decoupled from the housing 33. The housing 33 may include handles 43 (e.g., see FIG. 5A) that extend from the housing 33. The handles 43 may be positioned opposite to each other. In certain embodiments, the handles 43 may be positioned 180° apart along the circumference of the housing 33. The handles 43 allow for an ergonomic fit within a single hand of a user. The syringe-type configuration of the handles 43 allows single handed grip during advancement to both dwell and implantation.

Figure 5A:
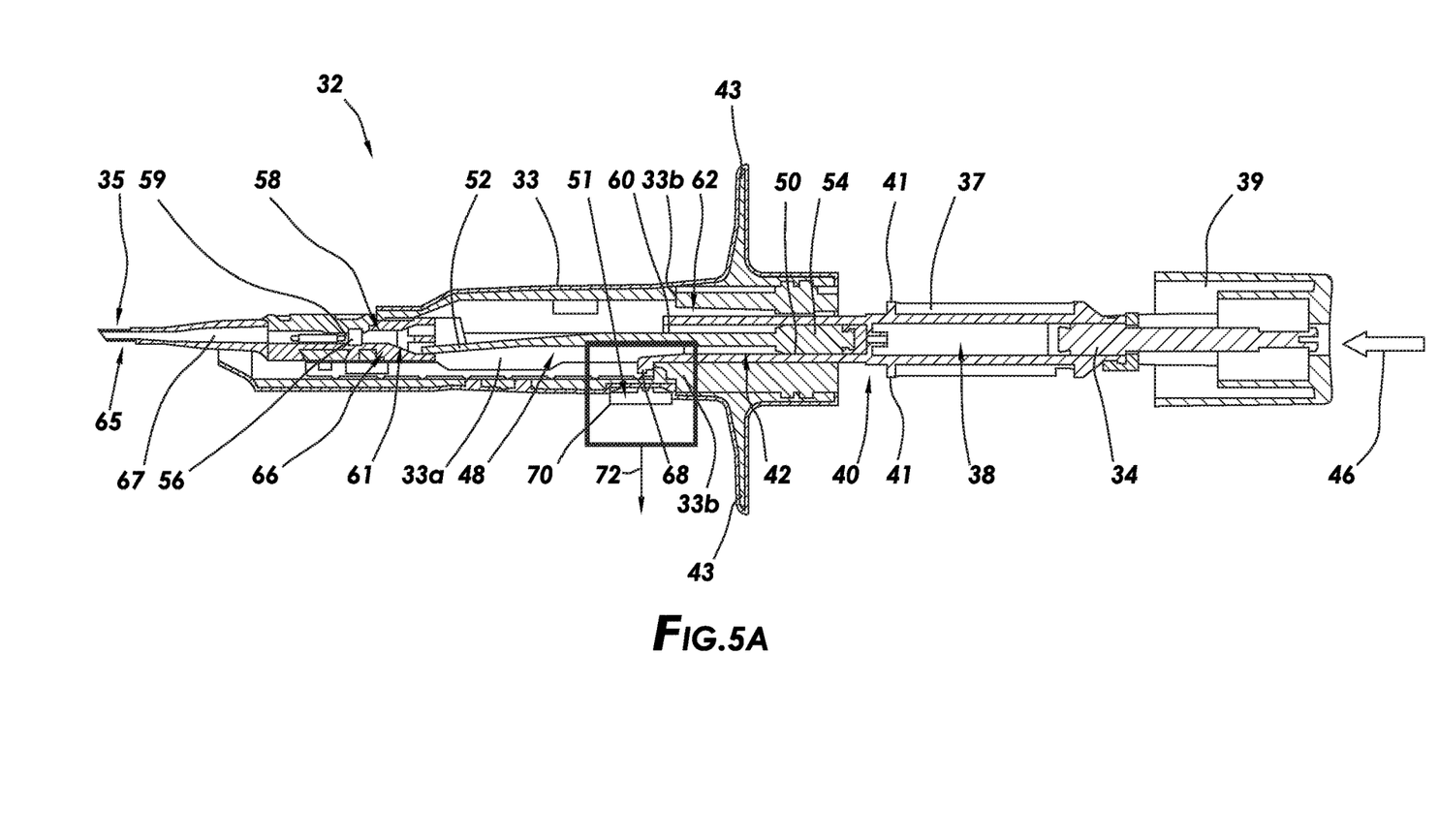
FIGS. 5A-5C are cross-sections of the top view of the insertion tool of FIG. 4.
Figure 5B:
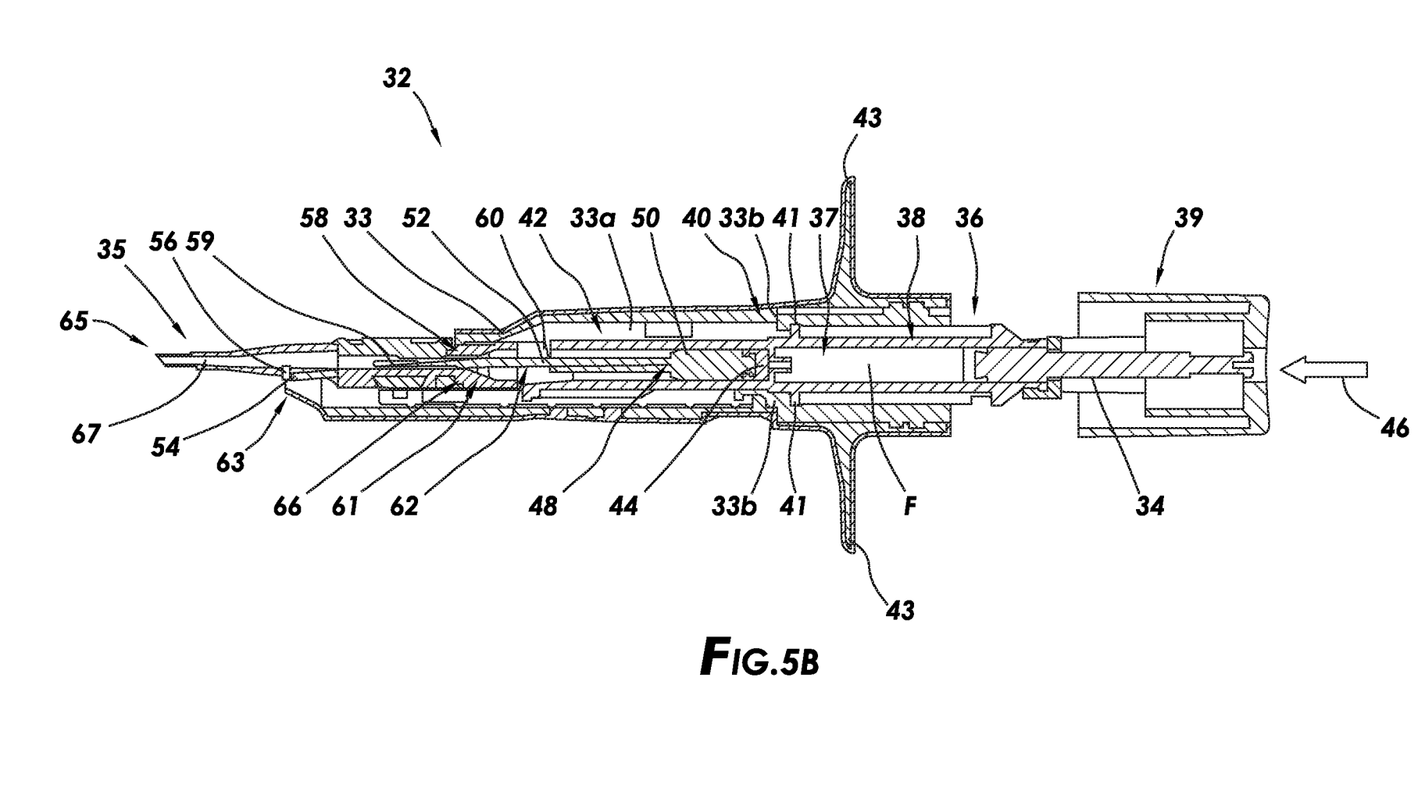
Figure 5C:
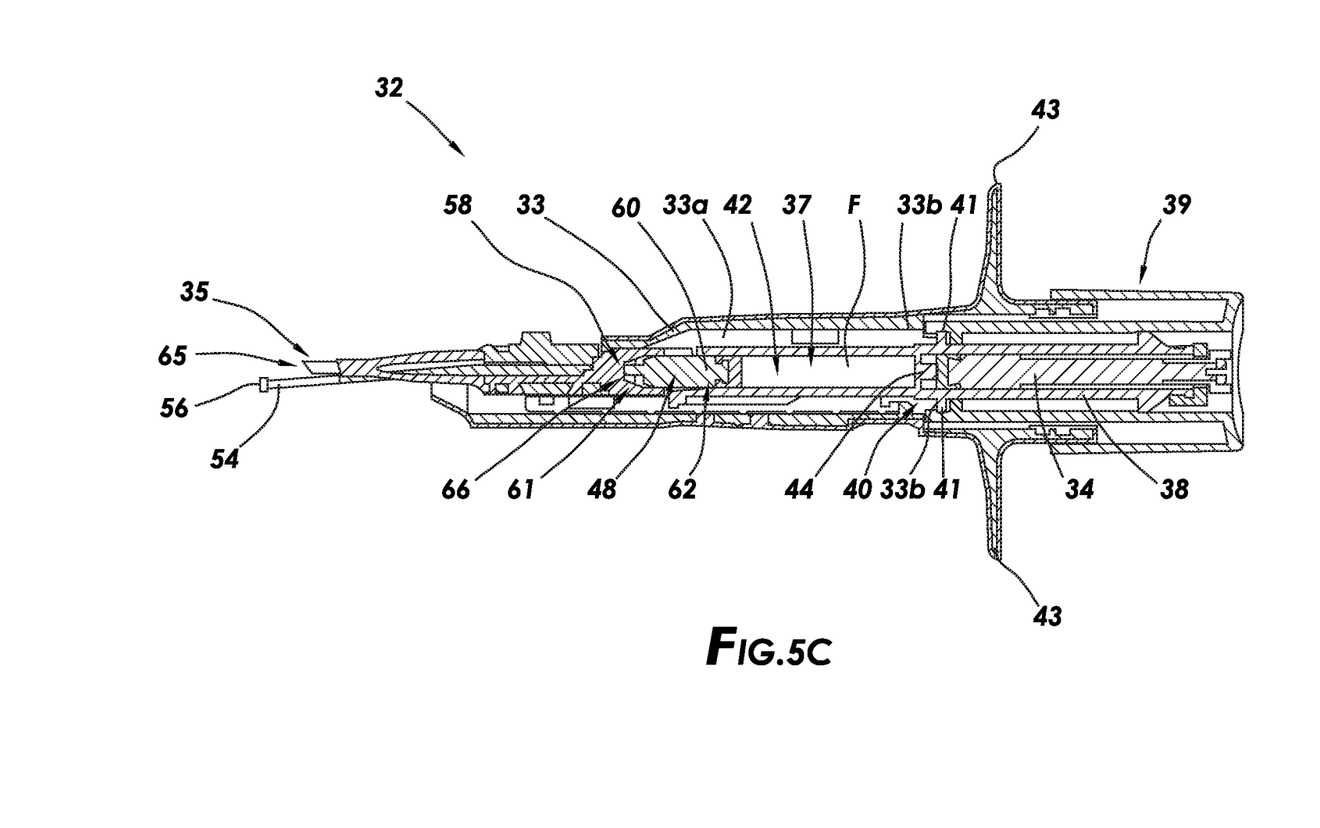

FIGS. 5A-5C are cross-sections of the top view of the insertion tool 32 of FIG. 4 in accordance with exemplary embodiments. The cross-sections are taken in a downward direction along the dashed line between A and A' (along an entire length of the insertion tool 32), as shown.

A first cylinder 38 and a second cylinder 42 may be movably disposed within the housing 33 (e.g., an interior portion of the housing 33 including a passage 33a, as shown). The first cylinder 38 may be adjacent to, coupled to, and/or axially aligned with the second cylinder 42, as shown. An orifice 44 may be positioned between the first cylinder 38 and the second cylinder 42 and may allow fluid communication between both cylinders. The first cylinder 38 may contain a hydraulic fluid F, such as a saline solution, for example. The second cylinder 42 is configured to receive the hydraulic fluid F from the first cylinder 38 via the orifice 44. That is, the second cylinder 42 is downstream to the first cylinder 38.

The plunger 34 may be at least partially disposed within the first cylinder 38. The plunger 34 may initially be positioned at a first end 36 of the first cylinder 38. The plunger 34 may be configured to move within the first cylinder 38 in an axial direction toward a second end 40 of the first cylinder 38, thereby displacing the hydraulic fluid F into the second cylinder 42 via the orifice 44, as the plunger 34 is depressed by a user. This axial movement is indicated by arrow 46.

The first cylinder 38 and the second cylinder 42 may allow a controlled fluid flow rate through the orifice 44 thereby regulating a maximum flow rate and thus regulating the maximum allowable speed of plunger travel. Regulating the plunger travel may prevent the IOL from traveling faster than a flow rate allowed by the cylinders 38, 42 and the orifice 44, regardless of an applied force to the plunger 34 by a user.

A shaft 48 may be disposed within the second cylinder 42. The shaft 48 may be configured to move axially within the second cylinder 42 as the second cylinder 42 receives the hydraulic fluid F. The shaft 48 may include a first portion 50 and a second portion 52, as shown. The outer diameter of the second portion 52 may be less than the outer diameter of the first portion 50.

The first portion 50 may be positioned closer to the orifice 44 than the second portion 52. The second portion 52 may be an elongated member including a distal end 54 configured to contact and move (e.g., push) a lens component 56. The lens component 56 may include at least one component of the modular IOL 10 shown on FIG. 2, such as the base portion 12 or the lens portion 14. The lens component 56 may be positioned within a bay 58 of the insertion tool 32, as shown.

The bay 58 may be a compartment that is positioned between the second cylinder 42 and the nozzle 35. The bay 58 may include a lumen 59 that is in fluid communication with a folding chamber 61 that is positioned in the bay 58, as shown. In at least one embodiment, the folding chamber 61 may include surface features (e.g., contours 66) or other topography configured to fold the lens component 56. In some embodiments, the lens component 56 may be folded and then placed into the folding chamber 61.

In certain embodiments, the bay 58 may be a detachable cartridge that may be coupled and decoupled to the housing 33. In other embodiments, the bay 58, may include the folding chamber 61 that includes surface topography (e.g., contours 66) used for folding the lens component 56 may be integrally formed in or a permanent part of the housing 33. In some embodiments, the bay 58 may contain the lens component 56. In some embodiments, the lens component 56 may be loaded in the bay 58 in an unfolded configuration. The bay 58 may be actuated to fold the lens component 56 for delivery via the nozzle 35. As used herein, folding of the lens component 56 is also intended to encompass rolling of the lens component 56. For example, the haptic extensions 18 of the base portion 12 shown on FIG. 2 may be folded onto the base 16, which may then be folded or rolled. By way of further example, the lens portion 14 shown on FIG. 2 may be folded or otherwise rolled into a folded configuration for delivery through the nozzle 35.

In some embodiments, the insertion tool 32 may be preloaded. That is, when provided to an end-user, the insertion tool 32 may have the lens component 56 (e.g., modular IOL 10, base portion 12, and/or lens portion 14) in an unfolded state already present there within and ready to deliver. Having the insertion tool 32 preloaded with the lens component 56 should reduce the number of steps a user may be required to accomplish before delivering the lens component 56 into a patient. With a reduced number of steps, error and risk associated with delivery of the lens component 56 into a patient may be reduced. Further, an amount of time required to deliver the lens component 56 may also be reduced. In some embodiments, the lens component 56 may be pre-loaded into the bay 58.

The lumen 59 may be aligned with a deployment channel 67 of the nozzle 35. The deployment channel 67 may receive the lens component 56 from the bay 58 during depression of the plunger 34. An opening 65 may provide an exit for the deployment channel 67 so that the lens component 56 can be delivered through the nozzle 35 into an eye. The nozzle 35 may be positioned adjacent to the bay 58. In some embodiments, the nozzle 35 (or a portion thereof) may be integrally formed in or a permanent part of the housing 33 and/or the bay 58.

The first portion 50 may initially be positioned adjacent to the orifice 44 prior to the plunger 34 moving the hydraulic fluid F from the first cylinder 38 into the second cylinder 42. The second portion 52 may extend through an opening 60 that is positioned at a distal end 62 of the second cylinder 42. As the plunger 34 is depressed and the second cylinder 42 receives the hydraulic fluid F, the shaft 48 is forced to move, causing the first portion 50 to move away from the orifice 44 (toward the opening 60) and causing the second portion 52 to move through the opening 60 and into the bay 58 to contact and move the lens component 56 axially. In other words, as the plunger 34 is depressed, the hydraulic fluid F is displaced from the first cylinder 38 into the second cylinder 42 via the orifice 44 and flows against the shaft 48 thereby moving the shaft 48 axially. The shaft 48 moves axially to contact and push the lens component 56 from the bay 58 through the folding chamber 61. The lens component 56 may continue to move through the lumen 59 and the deployment channel 67 and out the nozzle 35 (via the opening 65) for delivery into an eye.

Additionally, the first portion 50 may be configured (upon depression of the plunger 34) to form a seal upon contacting the opening 60, thereby preventing the hydraulic fluid F from entering the bay 58. Also, the distal end 62 may be configured as a physical stop to prevent axially movement of the shaft 48 beyond the distal end 62. That is, the diameter of the opening 60 may be less than the outer diameter of the first portion 50. The shaft 48 may continue to move until first portion 50 contacts the distal end 62 or when a user stops applying force to the plunger 34.

With reference to FIG. 5A, in an initial position, the lens component 56 may be positioned in the folding chamber 61 prior to the advancement stage. The folding chamber 61 is configured to fold or roll the lens component 56 with the contours 66. The lens component 56 may be rolled or folded to reduce a size of the lens component 56. This reduction in size allows delivery of the lens component 56 through a minimally sized incision in the eye.

With additional reference to FIG. 5B, in the advancement stage, the plunger 34 may advance the lens component 56 from the folding chamber 61 to a dwell position 63 in a deployment channel 67 of the nozzle 35. In some embodiments, the lens component 56 may be folded in the advancement stage. While the dwell position 63 is shown in the nozzle 35, the dwell position 63 of the lens component 56 may be otherwise situated, for example, in the bay 58.

With additional reference to FIG. 5C, in the deployment stage, the plunger 34 may advance the lens component 56 from the dwell position 63 and out the opening 65 of the nozzle 35 into a patient's eye.

The insertion tool 32 may also include a locking mechanism for a plunger assembly 37. The plunger assembly 37 may be movably disposed (e.g., axial movement) within the housing 33. In certain embodiments, the plunger assembly 37 may move axially upon depression of the plunger 34.

During a locked position, a member 68 may extend from the plunger assembly 37 and abut a tab 70 movably disposed within a recess 51, as shown on FIG. 5A. The plunger assembly 37 may include the plunger 34, the first cylinder 38, the second cylinder 42, the orifice 44, and the shaft 48. During the locked position, a first portion of the second cylinder 38 may extend out of the passage 33a and a second portion of the second cylinder 38 may extend into the passage 33a.

The tab 70 prevents axial movement of the plunger assembly 37 by preventing the member 68 from moving upon the plunger 34 being depressed (e.g., the plunger 34 may be in a locked or unlocked position). The tab 70 may be pulled away (indicated by arrow 72 on FIG. 5A) from the member 68 to disengage the member 68 and unlock the plunger assembly 37 and allow axial movement of the plunger assembly 37 upon depression of the plunger 34.

The plunger assembly 37 may include a protrusion 41 that extends circumferentially about an exterior surface of the first cylinder 38. The protrusion 41 is configured to contact a portion 33b of a passage 33a of the housing 33. The portion 33b may be an interior wall of the passage 33a that extends inward in a direction toward a longitudinal axis of the passage 33a. The portion 33b may prevent the plunger assembly 37 from moving beyond the portion 33b, as shown on FIG. 5C. For example, the portion 33b may be an inner ring that abuts the protrusion 41 that may be an external or outer ring. An outer diameter of a portion of the plunger assembly 37 that includes the protrusion 41 (e.g., the external ring) is larger than in inner diameter of the passage 33a at the portion 33b (e.g., the inner ring).

Figure 6:
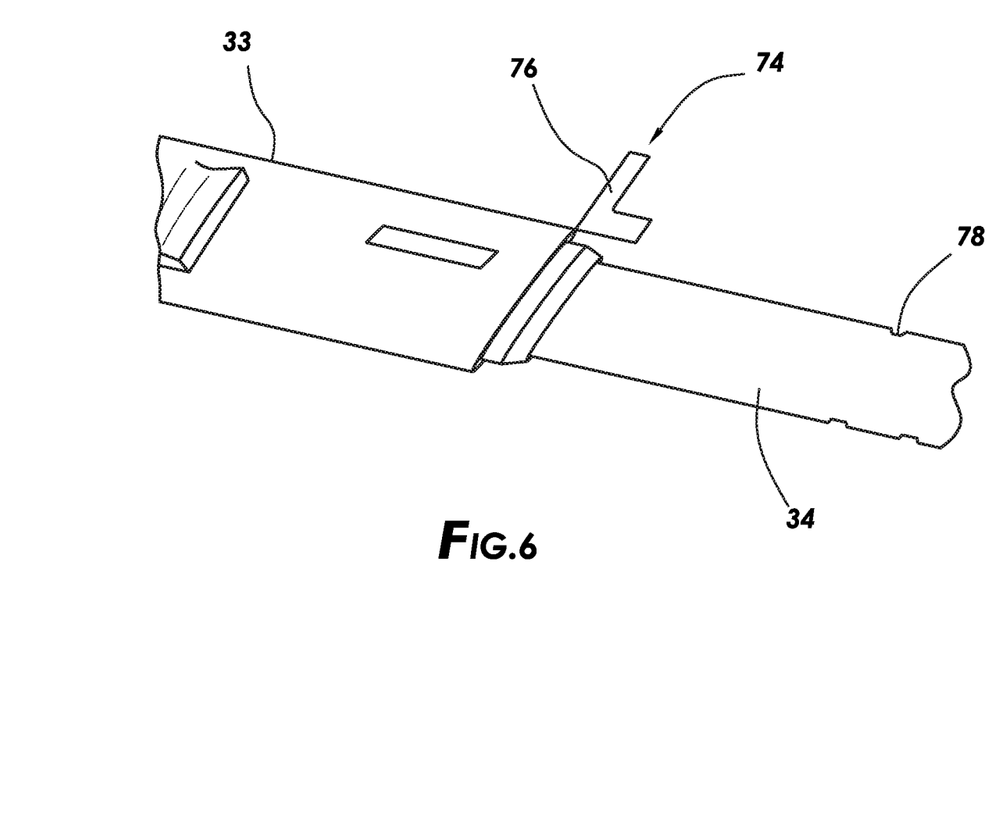
FIG. 6 illustrates a locking mechanism of an insertion tool in accordance with embodiments of the present disclosure.

In some embodiments, as shown on FIG. 6, the insertion tool 32 may include a locking mechanism 74 for the plunger 34. The locking mechanism 74 may be coupled to the housing 33 or that may be a separate component. The locking mechanism 74 may include a tab 76 that resembles the shape of the letter "L". The tab 76 may extend from the housing 33. During a locked position, the tab 76 protrudes into a groove 78 of the plunger 34, thereby preventing axial movement of the plunger 34 relative to the housing 33. For unlocking, the tab 76 is rotated away from the groove 78 (with a threshold amount of force) thereby allowing axial movement of the plunger 34. That is, the groove 78 may be configured to disengage from the tab 76 upon rotation of the plunger 34. As noted, a minimum amount of force may be utilized by a user to unlock or break free the tab 76 from the groove 78. This rotation removes the tab 76 from the groove 78 and may produce an audible sound including a "snap," "pop," or "click." This may alert a user that the plunger 34 is unlocked without the user viewing the insertion tool 32.

Figure 7:
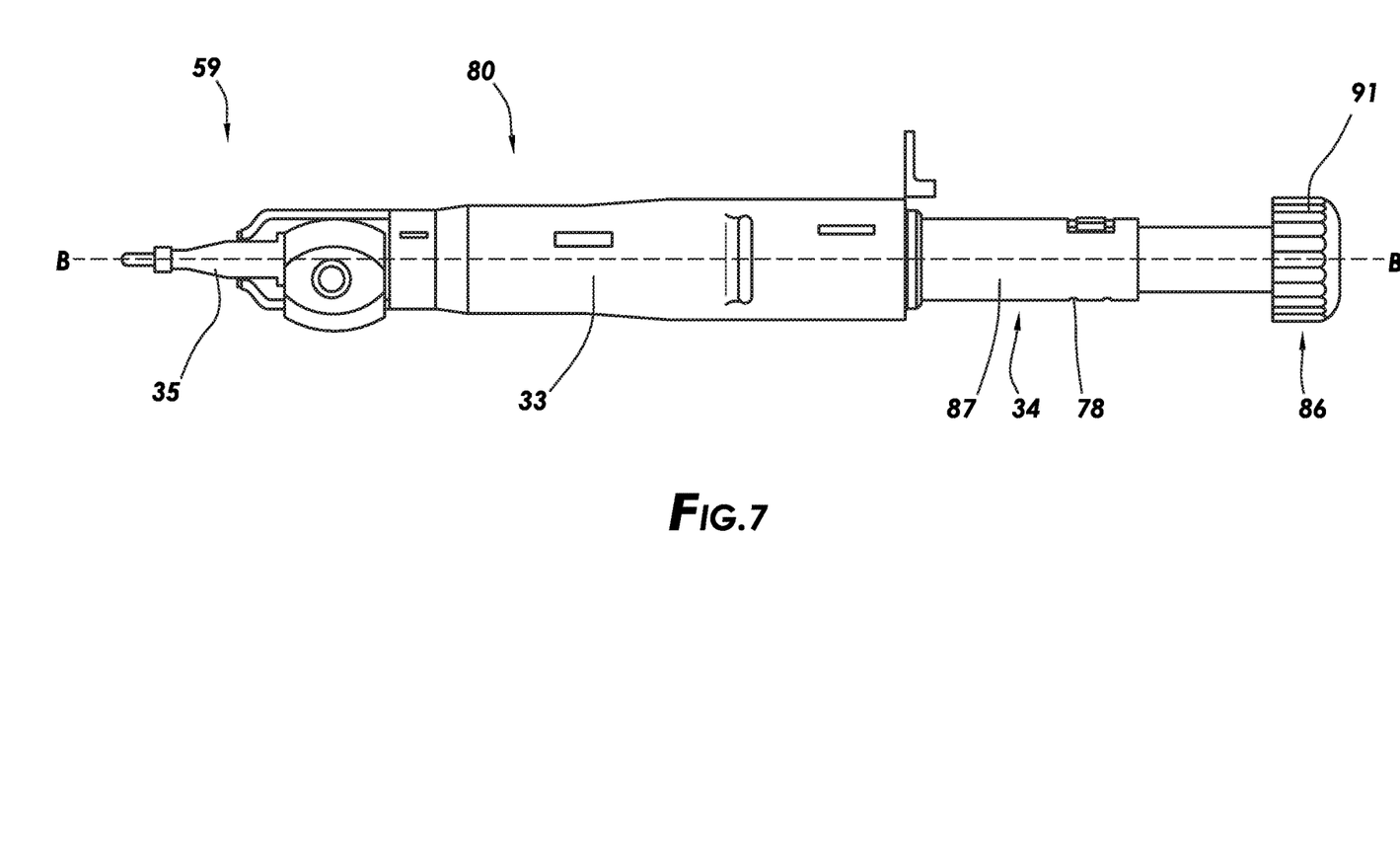
FIG. 7 is a top view of an insertion tool in accordance with embodiments of the present disclosure.
Figure 8:
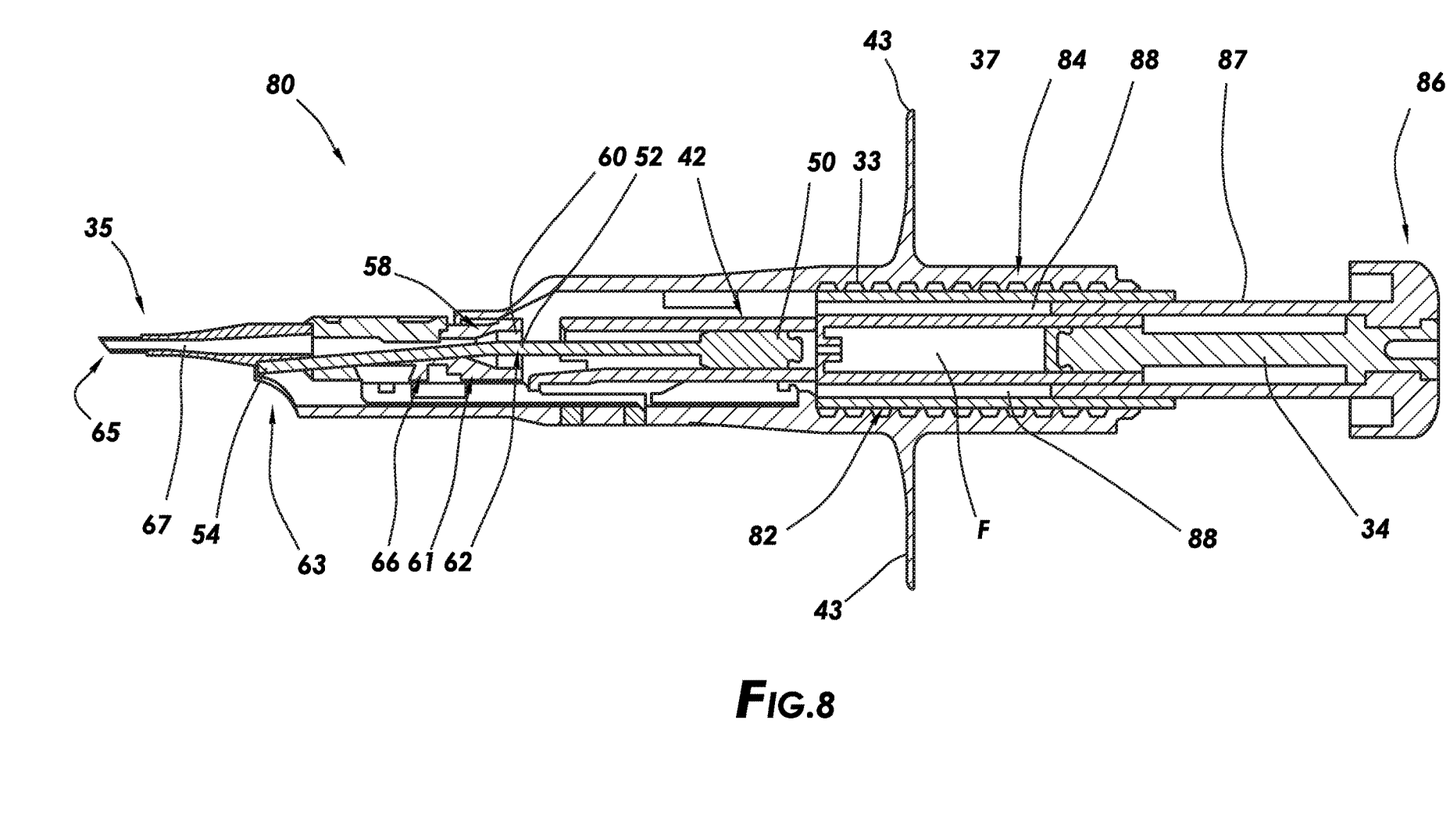
FIG. 8 is a cross-section of the top view of the insertion tool of FIG. 7 in accordance with embodiments of the present disclosure.

FIG. 7 illustrates a top view of an insertion tool 80 in accordance with exemplary embodiments. FIG. 8 is a cross-section of a top view of the insertion tool 32 of FIG. 7 in accordance with exemplary embodiments. The cross-section is taken in a downward direction along the dashed line between B and B', as shown. The insertion tool 80 may be similar to the insertion tool 32, however, the insertion tool 80 may include a threaded sleeve 82 that mates with a threaded portion 84 (e.g., a threaded passage) of the housing 33. The threaded sleeve 82 may be concentrically positioned within the threaded portion 84. The threaded sleeve 82 may be a tubular including exterior threads. The threaded portion 84 may be a tubular including interior threads configured to mate with the exterior threads of the threaded sleeve 82. The outer diameter of the threaded sleeve 82 is less than the inner diameter of the threaded portion 84. In other words, the threaded sleeve 82 screws into the threaded portion 84. This allows adjustment of the overall length of the insertion tool 80 to allow users with different hand sizes to utilize the insertion tool 80 with improved ergonomics, for example.

The plunger 34 may include a plunger head 86 that is attached to tubular portion 87, as shown. The plunger head 86 may be rotated to axially move the threaded sleeve 82 forward (or backward) along threaded portion 84, thereby moving the plunger assembly 37 axially. The plunger head 86 can also be rotated to unlock the insertion tools, as described herein. The threaded sleeve 82 may be coupled to the plunger assembly 37. The tubular portion 87 may be initially locked into place with at least one of the mechanisms, as described above (e.g., the locking mechanisms 68 and/or 74). This allows rotation of the threaded sleeve 82 by a user to adjust an overall length of the insertion tool 80. Once unlocked, the plunger head 86 may be depressed causing the tubular portion 87 to move along passage 88, as shown. The plunger head 86 may include ridges 91 to improve grip by a user (i.e., improved ergonomics).

An exemplary technique for implantation of the modular IOL 10 into an eye 90 of a patient will now be described with respect to FIGS. 9A-9C.

Figure 9A:
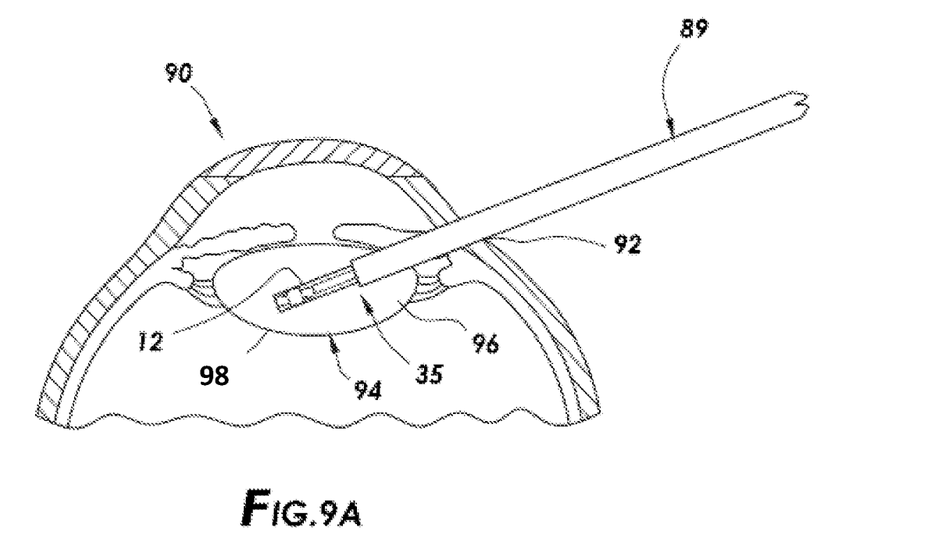
FIGS. 9A-9C illustrate implantation of a modular IOL in accordance with embodiments of the present disclosure.
Figure 9B:
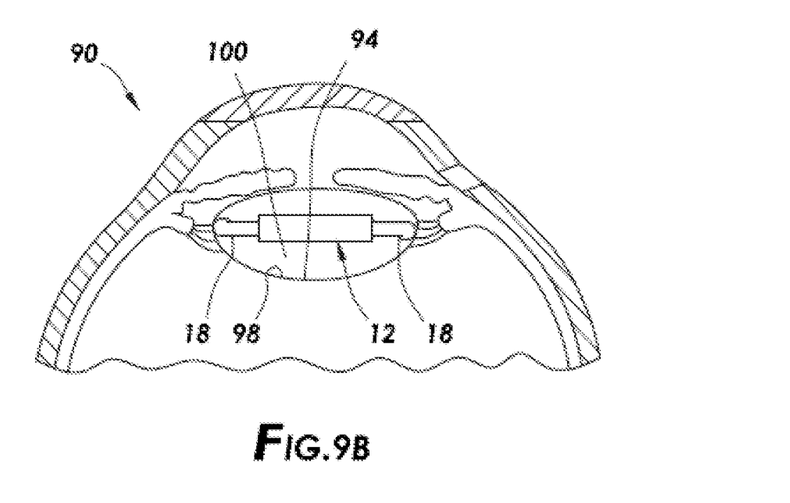

As illustrated on FIG. 9A, an insertion tool 89 (e.g., the insertion tool 32 or the insertion tool 80) may first dispense the base portion 12 into the eye 90 of a patient. In embodiments, an incision 92 may be made in the eye 90 by a surgeon. For example, the incision 92 may be made through the sclera 94 of the eye 90. The incision 92 may be a suitable width or length. Without limitation, the suitable width and/or length may be less than about 2000 microns (2 millimeters). For example, the incision 92 may have a suitable width and/or length of from about 0 microns to about 500 microns, from about 500 microns to about 1000 microns, from about 1000 microns to about 1500 microns, or from about 1500 microns to about 2000 microns. After the incision 92 is made, the nozzle 35 of the insertion tool 89 may be inserted through the incision 92 into an interior portion 96 of the eye 90. The insertion tool 89 may be actuated to dispense the base portion 12 into a capsular bag 98 of the eye 90. This initial movement of the base portion 12 may be performed at any suitable time, for example, before the incision 92 is made. Once the insertion tool 89 is positioned with the nozzle 35 in the eye 90, the insertion tool 89 may then drive the base portion 12 (in a folded or rolled configuration) through the nozzle 35 and into the interior portion 96 of the eye 90. Upon dispensation, the base portion 12 should unfurl and settle within the capsular bag 98 of the eye 90, as shown on FIG. 9B. The haptic extensions 18 may be manipulated, for example, to engage the inside equator 100 of the capsular bag 98. The haptic extensions 18 may engage the capsular bag 98 to secure the base portion 12 in the capsular bag 98.

Figure 9C:
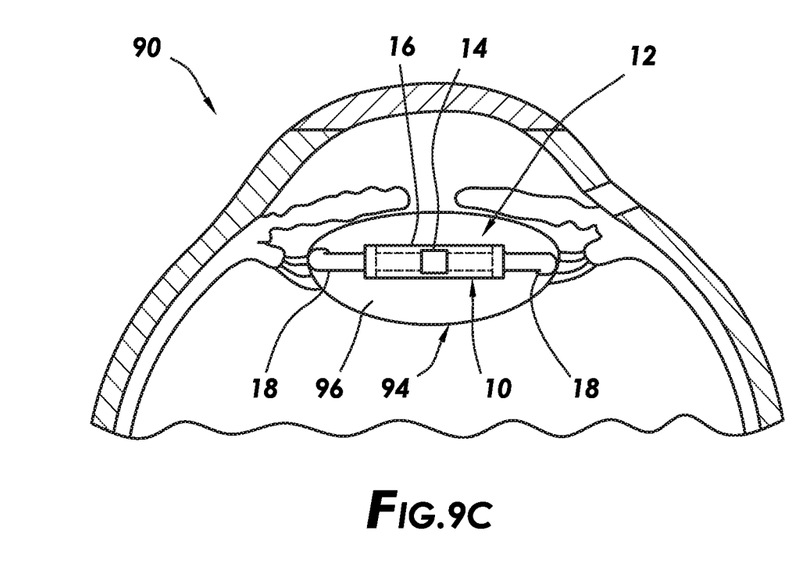

As illustrated on FIG. 9C, the lens portion 14 may be positioned in the interior portion 96 of the eye 90. In the illustrated embodiment, the lens portion 14 is shown positioned in the base 16 of the base portion 12. The lens portion 14 may be delivered in a folded (or rolled configuration) and allowed to unfurl after ejection from the inserter. The lens portion 14 may be positioned in the base 16 of the base portion 12 and secured to the base portion 12, for example, by use of the tabs 30 shown on FIG. 3, to form the modular IOL 10. However, embodiments should not be limited to use of the tabs 30 for interlocking the lens portion 14 and the base portion 12 and other suitable locking mechanisms may be used for securing lens portion 14 to the base portion 12 for forming the modular IOL 10. The base portion 12 may hold the lens portion 14 within the eye 90 so that the lens portion 14 may refract light to be focused on the retina.

Use of the methods and systems described herein may provide numerous benefits and advantages over other IOL delivery systems. For example, the insertion tool 89 including the preloaded IOL improves sterility due to decreased handling by users. Also, the insertion tool 89 can be utilized with one hand due to its ergonomic fit within one hand. A rotational mechanism to unlock the insertion tool 89 is an easy motion and the audible click provides feedback to users regarding insertion tool readiness. Further, a hydraulic mechanism (e.g., the first cylinder 38, the orifice 44, and the second cylinder 42) maintains a constant flow rate without varying a user's force input. This hydraulic mechanism provides a steady force feedback and limits occurrences of sudden ejection of the IOL. Also, the insertion tool 89 may allow a user to apply a reasonable amount of force against the plunger 34 throughout delivery of the IOL, thereby reducing any user fatigue.

It is believed that the operation and construction of the present disclosure will be apparent from the foregoing description. While the apparatus and methods shown or described above have been characterized as being preferred, various changes and modifications may be made therein without departing from the spirit and scope of the disclosure as defined in the following claims.

What is claimed is:

1. An apparatus for delivery of a lens component into an eye, comprising:
   a housing;
   a nozzle operatively coupled to the housing;
   a first cylinder movably disposed within the housing;
   a second cylinder movably disposed within the housing, wherein the second cylinder is in fluid communication with the first cylinder;
   a plunger at least partially and movably disposed within the first cylinder;
   a shaft movably disposed within the second cylinder, wherein the shaft is configured to move toward the lens component;
   a locking mechanism for the plunger, the locking mechanism including a tab, the locking mechanism configured such that:
      the tab protrudes into a groove of the plunger to prevent axial movement of the plunger relative to the housing when the plunger is in a locked position;

the tab is disengaged from the groove when the plunger is rotated, to unlock the plunger, to allow axial movement of the plunger relative to the housing, and further wherein the locking mechanism is configured to produce an audible sound output when the tab is disengaged from the groove to alert a user when plunger is unlocked.

2. The apparatus of claim 1, wherein the first cylinder comprises a hydraulic fluid.

3. The apparatus of claim 2, wherein the tab extends from the housing.

4. The apparatus of claim 3, wherein the second cylinder is positioned downstream to the first cylinder.

5. The apparatus of claim 4, wherein the apparatus further comprises a plunger assembly movably disposed within the housing, the plunger assembly comprising:
  the first cylinder;
  the second cylinder;
  the plunger; and
  the shaft,
  wherein the plunger assembly is configured to move axially, in a downstream direction.

6. The apparatus of claim 5, further comprising a second tab abutting a member extending from the plunger assembly, wherein the second tab is configured to disengage from the member to allow axial movement of the plunger assembly.

7. The apparatus of claim 6, wherein a bay is positioned between the nozzle and the second cylinder, wherein the bay is configured to receive a portion of the shaft.

8. The apparatus of claim 7, wherein the bay includes a folding chamber including contours configured to fold or roll the lens component.

9. An apparatus for delivery of a lens component into an eye, comprising:
  a housing comprising a threaded passage;
  a nozzle operatively coupled to the housing;
  a threaded sleeve disposed concentrically within the threaded passage; and
  a plunger assembly coupled to the threaded sleeve, the plunger assembly comprising:
    a first cylinder;
    a second cylinder, wherein the second cylinder is in fluid communication with the first cylinder;
    a plunger at least partially disposed within the first cylinder; and
    a shaft movably disposed within the second cylinder, wherein the shaft is configured to move toward the lens component
  and further comprising:
    a locking mechanism for the plunger, the locking mechanism including a tab,
    the locking mechanism configured such that:
      the tab protrudes into a groove of the plunger to prevent axial movement of the plunger relative to the housing when the plunger is in a locked position;
      the tab is disengaged from the groove when the plunger is rotated, to unlock the plunger, to allow axial movement of the plunger relative to the housing, and
      further wherein the locking mechanism is configured to produce an audible sound output when the tab is disengaged from the groove to alert a user when the plunger is unlocked.

10. The apparatus of claim 9, wherein the plunger comprises a groove configured to disengage from a tab upon rotation of the plunger to allow axial movement of the plunger, wherein the tab extends from the housing.

11. The apparatus of claim 10, further comprising a second tab abutting a member extending from the plunger assembly, wherein the second tab is configured to disengage from the member to allow axial movement of the plunger assembly.

12. The apparatus of claim 11, wherein the plunger comprises a cap configured to rotate the plunger assembly.

13. The apparatus of claim 9, wherein the lens component comprises a base portion of a modular intraocular lens or a lens portion of the modular intraocular lens.

14. The apparatus of claim 9, further comprising a bay positioned between the nozzle and the second cylinder.

15. A method for delivery of a lens component into an eye, comprising:
  providing an insertion tool, wherein the insertion tool comprises:
    a housing;
    a first cylinder movably disposed within the housing, wherein the first cylinder comprises a hydraulic fluid;
    a second cylinder movably disposed within the housing, wherein the second cylinder is in fluid communication with the first cylinder;
    a plunger at least partially disposed within the first cylinder; and
    a shaft movably disposed within the second cylinder, wherein the shaft is configured to move towards the lens component; and
  actuating the plunger to move the hydraulic fluid from the first cylinder into the second cylinder to axially move the shaft to drive the lens component in the nozzle,
  wherein the plunger further comprises:
    a locking mechanism for the plunger, the locking mechanism including a tab,
    the locking mechanism configured such that:
      the tab protrudes into a groove of the plunger to prevent axial movement of the plunger relative to the housing when the plunger is in a locked position;
      the tab is disengaged from the groove when the plunger is rotated, to unlock the plunger, to allow axial movement of the plunger relative to the housing, and
      further wherein the locking mechanism is configured to produce an audible sound output when the tab is disengaged from the groove to alert a user when the plunger is unlocked.

16. The method of claim 15, wherein the housing further comprises a threaded passage and a threaded sleeve disposed concentrically within the threaded passage.

17. The method of claim 16, wherein the threaded sleeve is coupled to a plunger assembly, the plunger assembly comprising:
  the first cylinder;
  the second cylinder;
  the plunger; and
  the shaft.

18. The method of claim 17, wherein the plunger comprises a cap configured to rotate the plunger assembly.

19. The method of claim 18, further comprising rotating the threaded sleeve to move the plunger assembly along the threaded passage.

20. The method of claim 19, wherein the lens component comprises a base portion of a modular intraocular lens or a lens portion of the modular intraocular lens.

\* \* \* \* \*